United States Patent [19]

Diamond et al.

[11] 4,295,473
[45] Oct. 20, 1981

[54] APPARATUS AND METHOD FOR ANALYSIS OF MOTION OF A DYNAMIC STRUCTURE

[76] Inventors: George Diamond, 2408 Wild Oak Dr., Los Angeles, Calif. 90068; James Forrester, 3226 Serra Rd., Malibu, Calif. 90265; Michael Hirsch, 756 Amalfi Dr., Pacific Palisades, Calif. 91272; Ran Vas, 17130 Clemons Dr., Encino, Calif. 91436

[21] Appl. No.: 42,247

[22] Filed: May 24, 1979

[51] Int. Cl.³ .............................................. D61N 5/00
[52] U.S. Cl. .................................................... 178/695
[58] Field of Search ................................ 128/660–666, 128/668, 687–689, 691, 694–695, 700, 713, 721, 774, 778, 780, 782; 73/DIG. 11; 356/434–436, 373, 379, 385

[56] References Cited

U.S. PATENT DOCUMENTS

| 3,036,568 | 5/1962 | Stark | 128/664 |
| 3,361,128 | 1/1968 | Colman | 128/687 |
| 3,442,264 | 5/1969 | Levitt | 128/712 |
| 3,678,922 | 7/1972 | Phillips et al. | 128/692 |
| 3,684,378 | 8/1972 | Lord | 356/434 |
| 3,915,156 | 10/1975 | Wastl et al. | 128/688 |
| 3,929,125 | 12/1970 | Barnes et al. | 128/702 |
| 4,006,737 | 2/1977 | Cherry | 128/712 |
| 4,101,961 | 7/1978 | Fletcher et al. | 128/695 |
| 4,157,708 | 6/1979 | Imura | 128/666 |

FOREIGN PATENT DOCUMENTS 959214 2/1957 Fed. Rep. of Germany ...... 128/695

Primary Examiner—William E. Kamm
Attorney, Agent, or Firm—Robert J. Schaap

[57] ABSTRACT

An apparatus and method in which the amount of movement of a boundary in one or more dimensions on a dynamically movable structure or a series of sequential visual representations of said structure is measured. The boundary movement is measured by the degree of shiftable movement between light and dark areas. The motion may be analyzed and quantified in terms of linear motion or area change and an electrical analog of such motion is generated in format suitable for recordation by conventional reproducing or display mechanisms, as for example, a conventional chart recorder. In one embodiment, movement in one dimension, e.g. a linear dimension, is detected but not necessarily quantified. In another embodiment, the movement in the linear dimension is detected and measured so as to provide a quantification thereof. In a further embodiment the movement is measured in at least two dimensions to provide quantification of area changes. With suitable mathematical calculation, the area change with respect to an object of generally known shape can be converted for volume analysis. The apparatus comprises an electro-optical system including a plurality of photocells such as silicon photocells, and appropriate analog computation circuitry produces an electrical signal, as an analog of such dynamic motion, which when applied to a display screen, as for example a television tube, may display an ultrasonogram or a videofluoroscopic image.

58 Claims, 18 Drawing Figures

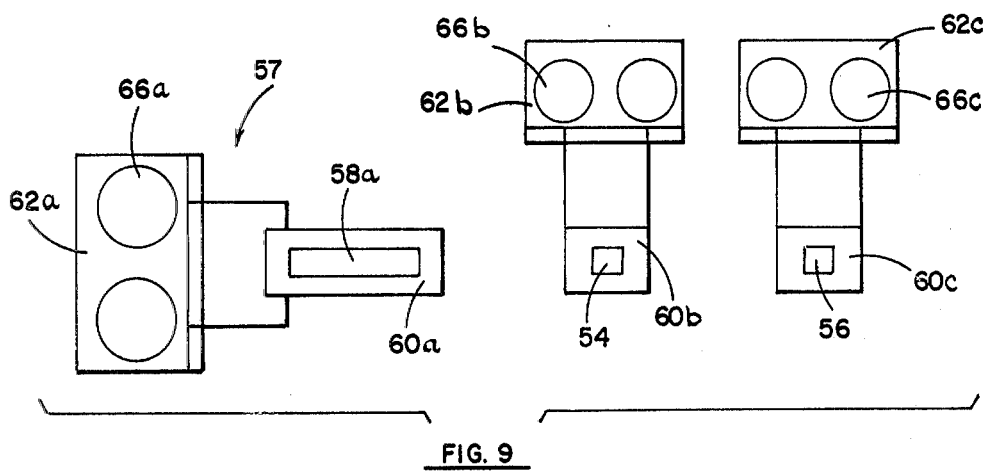
FIG. 9
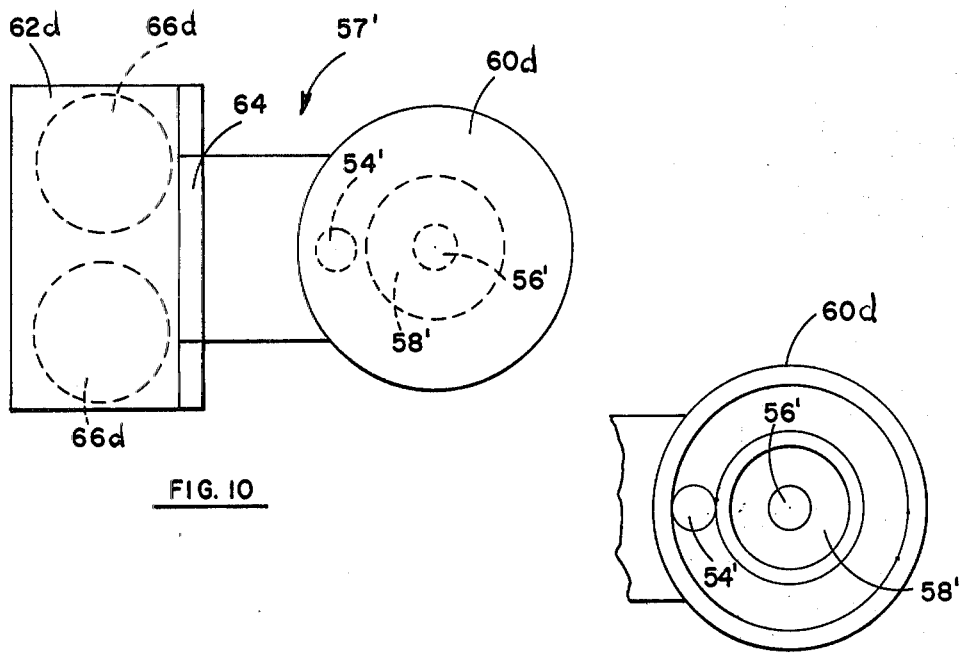
FIG. 10
FIG. 11
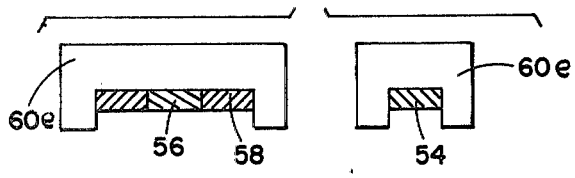
FIG. 12
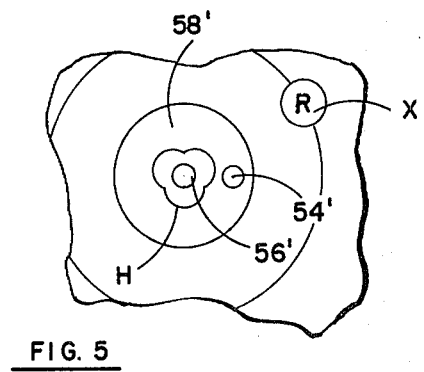
FIG. 5

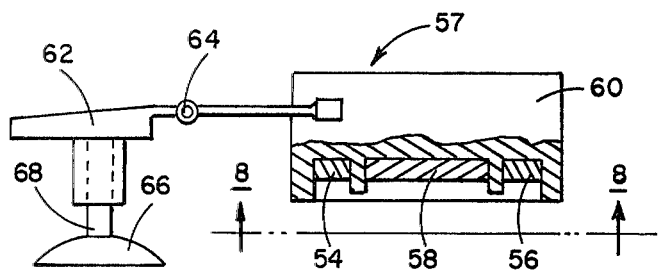
FIG. 6
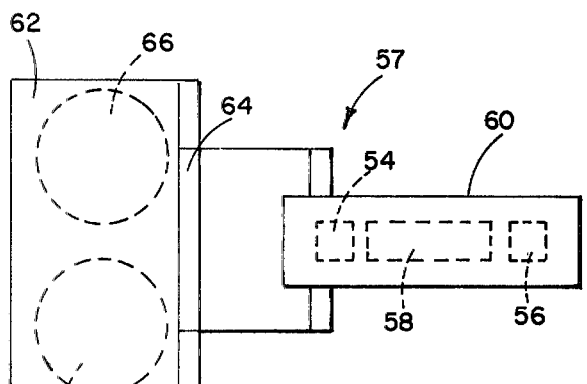
FIG. 7
FIG. 8
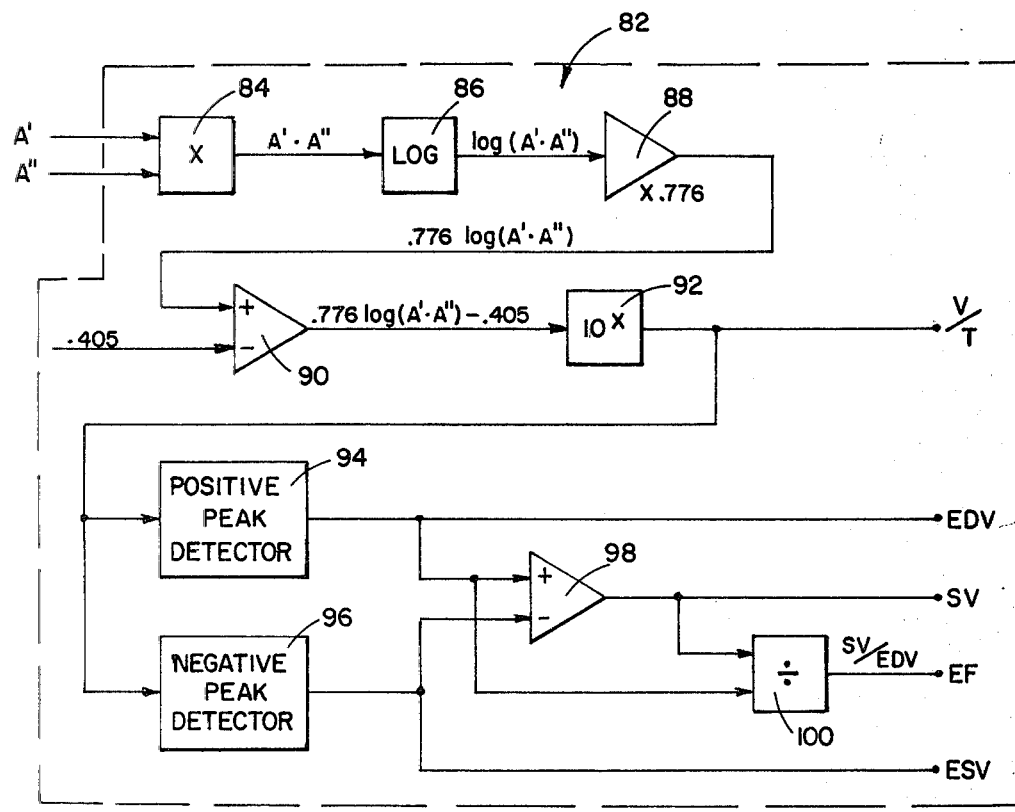
FIG. 15

APPARATUS AND METHOD FOR ANALYSIS OF MOTION OF A DYNAMIC STRUCTURE

BACKGROUND OF THE INVENTION

This invention relates in general to certain new and useful improvements in analysis of boundary movement of a dynamically movable structure or portrayed dynamic motion of said structure, and, more particularly, to the analysis of body tissue or a series of sequential images of the body tissue. More specifically, the present invention involves the analysis of video fluoroscopic images to provide a noninvasive means for detection and functional evaluation of clinical ischemic heart disease by a technique termed photokymography.

The photokymograph, often referred to as a "PKG", may be used to obtain both quantitative and/or qualitative records, not only of cardiac movement, such as sequential ventricular wall motion, but also of hemodynamic parameters such as instantaneous volumes, stroke volumes and ejection fractions. The photokymograph is applicable to any system producing a moving cardiac image, such as cineangiography, videofluoroscopy, two-dimensional ultrasonography and gated nuclear blood pool imaging. The photokymograph is directly able to detect and measure the linear motion of cardiac valves and also provide planimetric measurement and analysis of parameters such as ventricular volume, stroke volume, and ejection fraction.

In recent years, the increasing death rate in the population as a whole from cardiovascular disease has brought about a great increase in development of cardiovascular diagnostic equipment and techniques. One of the techniques which is used to measure cardiac output is angiography where a dye is injected into the heart by means of a catheter and the passage of the dye throughout the circulatory system is measured by colorimetric examination of the blood.

This latter technique is quite accurate and is the standard against which other diagnostic systems are measured. However, there is a significant risk to the patient with mortality/morbidity rates as high as four percent reported. Another method in current clinical use for measuring cardiac motion relies upon a radiopaque substance which is introduced into the heart by similar means and the cardiac motion is followed by roetgenography. The patient risk with this technique is less than dye injection because smaller volumes of foreign material are introduced. Measurement of stroke volume and other volumetric quantities has not been practical in most cases due to the complexity thereof.

More recent improvements in X-ray equipment and improved measurement techniques relied upon the substitution of an image intensified tube for the traditional film or fluoroscopic screen. The image obtained on the image intensified tube is then examined by television techniques which are very sensitive to low radiation levels. These improvements have made possible a great reduction in the exposure of the patient to potentially harmful radiation.

More recently there has been a surge in the development of sonar related techniques wherein a beam of ultra-sound is aimed through the area to be examined and the resultant echoes, after computer treatment, have been used to form a picture of the heart or other internal organs of a living human patient on a television screen. One further imaging system involving autoradiography has been developed to provide similar, photo evaluation of cardiac activity. Autoradiography is used in such imaging by injecting a radioactive material, such as technetium, into the blood stream and capturing the resulting pattern of gamma ray radiation from the patient, by a gamma camera including a scintillation crystal and photomultiplier array. After electronic analysis and computer data reduction, the resulting picture can be displayed upon the face of a television screen. The random nature of the radiation events which comprise the elements of the image requires that the image be constructed over a significant time period. The image quality is a direct function of time for a given patient exposure to the radiation. This technique precludes the use of such systems to produce a real time or single beat cardiac measurement.

The images formed by these methods provide a large amount of diagnostic data to the cardiologist by direct viewing. However, precise measure of the motion of the heart as a whole, or portions thereof, can only be performed indirectly. One such method which may be used with a filmed examination of the X-ray image, or "cineangiography", has been to directly measure the image projected onto a translucent screen with dividers or the like, on a frame-by-frame basis. This technique is costly and slow and because it cannot be performed in real time and oftentimes results in poor or incomplete measurements, requiring the patient to undergo a second examination. A second method which is generally only applicable to television type images is called videotracking or "radarkymography". In this technique, the televised fluoroscopic images of a beating heart are used in conjunction with complex and specialized electronic equipment to detect the epicardial ventricular boundary. A voltage proportional to the instantaneous position of the ventricular boundary is generated, and after processing, is transmitted to a strip chart recorder for print-out. This technique is costly and complex. Further, this technique is limited by the nature of the image processing of the video images, due to the fact that the motion to be measured must lie perpendicular to the vertical axis of the video display tube and substantially parallel to the raster lines in the video display tube. Any angular difference between the desired perpendicularity will result in an induced measurement error from geometric causes. The fact that the normal motion of the heart caused by the diaphragm and the rotational component of the systolic contraction is present limits the accuracy which can be realized by this technique. The technique is further limited by an inherent time lag of from forty to fifty milliseconds which produces a significant reduction in high frequency response.

Still another method in common use is "videodensitometry". In this method an area controllable by the operator of the image is brightened by electronic means. This brightened area which constitutes a data "window" is placed over the area of interest so that the window is divided by the image into a bright and dark area which is the boundary of interest. Motion of the boundary will then alter the bright to dark area ratio and produce the requisite data signal. This technique, like videotracking, is limited to video images and suffers from cost, complexity and insensitivity to overall contrast changes such as those which occur during the washout of the contrast medium. Additionally, the control of the "window" position requires a high degree of dexterity and skill on the part of the operator who must hold the window in exact geometric relationship with the movement of the portion of the image to be scanned.

OBJECTS OF THE INVENTION

It is, therefore, the primary object of the present invention to provide an apparatus for detecting and measuring movement in at least one dimension of a portion of a dynamic structure or images of portrayed dynamic motion of said structure through photocell transducer detection and providing an electrical analog signal representative of such motion.

It is another object of the present invention to provide an apparatus of the type stated which is especially useful for dynamic analysis of body tissue or sequential images of such body tissue.

It is a further object of the present invention to provide an apparatus of the type stated which is also especially useful as a non-invasive means for the detection and functional evaluation of clinical ischemic heart disease through photokymography.

It is also an object of the present invention to provide a method of cardiac imaging permitting measurements to be made irrespective of image source generation and display geometry, as long as the image can be transilluminated in substantially planar form.

It is another salient object of the present invention to provide a means for tracking and quantifying structural movements at any point on the image and along any axis of the image.

It is still another object of the present invention to provide an apparatus of the type stated in which measurements can be made in the presence of varying contrasts and gamma ratios in an image or series of images which are examined.

It is still a further object of the present invention to provide a method of analyzing movement of a dynamic structure or images of portrayed dynamic motion of such structures with photocell transducer detection.

With the above and other objects in view, our invention resides in the novel features of form, arrangement and combination of parts presently described and pointed out in the claims.

GENERAL DESCRIPTION

The photokymograph of the present invention makes use of photocells and preferably silicon photocells for analysis of motion or a series of sequential images of the motion and conversion to a desired electrical analog.

In general, the photokymograph of the present invention is useful for analyzing images of portrayed dynamic motion, as for example, shiftable devices about which determinations are to be made, as for example, a reciprocatively shiftable drop hammer, or the like. The present invention is especially useful in image analysis of body tissue in a dynamic state and preferably cardiac and related tissues, although the invention is not so limited. Thus, the invention can be used in making measurements on any dynamic structure. The dynamically movable structure is one which is moving through its own force or with force provided to the structure from a source of energy.

The term "photokymograph" is used herein to represent the apparatus or the process of the present invention and involves the photometric transducer system of the present invention in a form where it is capable of interfacing with any existing optical system for the analog representation or quantification of kinetic activity.

In one embodiment of the invention, boundary motion of a structure or a series of sequential images thereof can be detected or measured and an electrical analog signal representative of the movement is generated. When a photocell of rectangular form, generally thin in the transverse dimension, is placed over a moving boundary between lighter and darker areas of a structure, such as a ventricular wall or a plurality of sequential images of the ventricular wall, the resulting output is a linear electrical analog of the motion. In this embodiment of the invention, the measurement of movement of the boundary across light and dark regions is not necessarily calibrated. However, in many cases, this is not necessary since only the relative values are needed.

This electrical analog is useful in comparing against a standard, or against previous electrical analogs of the same region, or against electrical analogs of different portions of the ventricular wall. In this respect, the measurement is only a relative measurement such that amplitudes of the various wave forms, for example, may be compared. However, the measurement is not necessarily a quantitative measurement, as described in more detail hereinafter.

As indicated previously, measurement and detection of boundary movement can be made on the actual structure itself, such as the body tissue, or otherwise a series of sequential images showing the movement of the structure. Thus, for example, the series of sequential images may be those of a motion picture of the moving boundary. Otherwise, the sequential images may be displayed on a television display screen or the like. Essentially, any means for displaying images of the structure in movement, at least in the region to be measured, may be employed.

As used herein, the term "boundary" may represent any part of the structure and is not limited to an edge portion on the structure. Thus, for example, the boundary may represent a portion of the structure such as a portion of the ventricular wall which exists between a light and a dark region and which is movable relative to the light and dark regions.

In another embodiment of the invention, the same detecting photocell may be employed to detect and measure the movement of a boundary across light and dark regions and where the measurement can be calibrated with respect to the brightness of the two light levels from the light and dark regions. In accordance with this embodiment of the invention, two reference photocells are used along with the detecting photocell. The detecting photocell is that cell which actually detects and measures the movement of the boundary, and the reference photocells detect the differences in light output from the dark and light areas. This one reference photocell may be located over the light area and the other of the reference photocells may be located over the dark area. With suitable circuitry hereinafter defined to compensate for changes in contrast, the differences in light levels of the light and dark areas may be calibrated.

In a further embodiment of the invention, planimetric detection and measurement can be made on a portion of a movable structure of a series of sequential images representative of the movement of that portion of the structure. Thus, if a large photocell is placed over a section of the areas in which the lighter and darker portions are in motion, such as the image of a filling and emptying a ventricle, the resultant output signal would be a fairly accurate analog of the planimetric area changes taking place beneath the photocell. For this purpose, large area, generally circular photocells may be employed. In addition, a plurality of such measurements can be made simultaneously from separate areas of the image being examined with separate detecting photocells. Consequently, the biplane ventricular cross-sectional areas can be readily measured by two or more of such detecting photocells.

The addition of a pair of smaller reference cells along with this single cell transducer, in the manner as previously described, can provide a reference level for the lighter and darker areas. The signals from these reference photocells provide the information required to permit compensation for changes in contrast between these areas and permits calibration in the recording.

In the non-calibrated system of the present invention, and even in the calibrated system of the present invention, the measurement is not quantitative in the absolute sense, inasmuch as the circuit which produces the analog signal in response to the signal from the photocell does not recognize magnitude of a movement. For example, when a signal from a detecting photocell is processed and uncalibrated with respect to dark and light levels, a difference in brightness between the dark and light areas and the difference in contrast will result in signals having greater and lesser amplitudes. The display of the analog signal, as for example, on an oscilloscope, does provide a signal which can be determined in the context of its magnitude, e.g. one volt per millimeter of movement. However, when measuring the boundary movement on a series of photographs or other series of sequential images thereof, the distance from the source producing the image to the actual structure may not be known. Consequently, the exact or absolute measurement cannot be determined with the system of the present invention. However, compensation for the distance between the source producing the images and the structure can be made. Thus, the term "measurement", as used herein, is used in a sense where absolute values are not determined, but only relative values given a specific amount of light impinging on the detecting photocell from the light and dark regions and with a given contrast between the light and dark regions. However, in the relative sense, the systems of the present invention can provide both qualitative (non-calibrated) and quantitative (calibrated) information.

Planimetric area measurements and linear measurements are essentially made in the same manner. The photocell used for making linear measurements would actually render a signal representative of an area, except for the fact that it is quite thin in the dimension transverse to the movement of the boundary across the photocell. In each case, the photocell is actually measuring the total amount of light received from the light and dark regions of the structure, or the series of sequential images of the structure. The total light impinging on the photocells active surface will change as the boundary moves back and forth across the light and dark regions. Thus, the light change is detected by the photocell as a result of boundary movement back and forth across the light and dark regions of the structure or series of sequential images.

In planimetric measurements, the area being measured will have a boundary which moves relative to the light and dark regions. Considering the outline of the cardiac wall in one plane, the periphery thereof may define a dark region within the cardiac wall periphery and the region beyond may represent the light region. As the cardiac muscle expands and contracts, the periphery thereof, representative of the boundary, will also expand and contract. Thus, the periphery of the cardiac wall, for example, represents a boundary which moves relative to the dark and light regions.

The electronic circuitry used in conjunction with the photocell or transducer first converts the electrical output from the photocell from a current output to a voltage output. This conversion is accomplished in a circuit having an integrated circuit operational amplifier where the current from the photocell is applied to a summing node, together with feedback via a resistor selected for scaling to provide a convenient range of voltage. Because the television image is constructed by a single rapidly moving point, the image is not constant even though to the eye it appears to be constant due to the phenomenon of persistence of vision.

The phenomenon of persistence inherent in human vision causes these individual images on a television tube to be blended together. To a human observer they are indistinguishable from an actual continuous moving image. A cinema image is also an intermittent one, but on a frame by frame basis, as opposed to an element to element basis in the television image. The response time of a silicon photocell, however, is so rapid that each of the individual still pictures, and each element within these pictures, is detached from the black interval between pictures. This would produce an undesirable flicker or artifact in the data records so obtained.

Depending on the image source being used, motion pictures, television, or the like, the flicker rate is generally in the range of 30 to 60 hertz. The signal from the current-to-voltage converter stage is then sampled synchronously with the flicker inherent in the source data by means of a conventional sample and hold circuit, each sample being taken synchronously with the image from the original data source. This produces a series of steps of amplitude which contain a significant amount of the flicker frequency which would result in objectionable artifact. Consequently, the sample and hold circuit is followed by a fourth order low-pass filter with a 3 db point at 20 hertz when used with television images. When configured for use with reverse projected cinema images, the filter response is reduced to 10 hertz to compensate for the lower frame rate as compared to the wide standard of 60 fields and 30 frames per second. This circuit will attenuate and, in effect, integrate the flicker component contained in the sample and hold output and effectively remove this artifact from the signal.

The low-pass filter is then followed by a conventional inverter, which may be bypassed by means of a switch, so that dependent upon the switch position, the image selected may be black on white or white on black for a particular desired output format. This switch permits determination of the direction of deflection of the galvanometer in a chart recorder which is used to provide a permanent record of the data being analyzed by this invention.

In the embodiments where calibration for image intensity variation is provided, analog computation means follows the selective inversion of the signal. The analog computation means compensates for image intensity variation due to medium wash-out or changes in the contrast of the original pictorial source. Considering a photocell of a total area A, if this photocell is uniformly illuminated with illumination of an intensity I, then the electrical signal S can be computed by the formula:

$$S = k + I + A \quad (1)$$

where k represents a constant of proportionality which is an inherent characteristic of the silicon photocell. Now considering a photocell in which one portion of area A' is illuminated at a level I' and the remaining area, A—A', is illuminated at a level I", then, the electrical signal S can be computed by the following formula:

$$S = k[(A'I') + (A - A')I''] \quad (2)$$

and by arrangement $$A' = \left( \frac{\frac{S}{k} - AI''}{(I' - I'')} \right) \quad (3)$$

where k is described above. This latter model describes the general case where a portion of the photocell area A' overlies the image of the ventricle, and the remaining portion A—A' overlies the myocardium and lung field. The model does not require that either region be totally black or totally white, but only that they have differing intensity levels.

The electrical analog of the values of I' and I" are derived by means of the ancillary or reference photocells mounted adjacent to the measuring photocell so that one of these ancillary photocells is measuring the generally lighter area for average intensity, and the second is measuring the generally darker region for average intensity. Alternatively, the reference photocells can be located remotely from the detecting photocell but located in a region of the image or the structure having equivalent light and dark intensity levels. These signals from the reference photocells then provide the electrical analog of the I' and I" terms of the equation. The two signals derived from these two photocells are then summed in a conventional operation amplifier circuit to provide a measure of average illumination which will be used to compensate the output data signal from the detecting photocell for changes in illumination of the scene being examined by the system so that the change of output due to gamme shift or the like may be removed from the data. The signal from one of these reference photocells is amplified in a conventional operational amplifier circuit which performs the current-to-voltage conversion previously described. This signal is then summed in a conventional operational amplifier circuit with the output signal of the low-pass filter previously described. This signal is then applied to a conventional analog divider circuit at the dividend input with the previously summed reference photocell outputs as the divisor in the same analog divider circuit. The quotient output from this circuit may be the electrical analog of instantaneous area and is applied to the input of the strip chart recorder to provide a continuing record of the boundary movement being measured by the invention.

Calibrated planimetric measurements of changes of area can be made by a similar technique. The detecting photocell is selected to have a large enough active surface area to effectively cover that portion of the image to be examined for area change. The detecting photocell is provided with a substantially centrally located aperture for receiving one of the two reference photocells. The second reference photocell is attached to the periphery of the detecting photocell, or, otherwise, one or both of the reference photocells may be located with respect to the structure or the images thereof independently of the detecting photocell as previously described. This construction provides the means whereby the two reference levels required for calibration are provided. It can be seen that changes of illuminated area will provide a change in signal output from the photocell applied to the image in essentially the same manner as previously described for making measurements of linear motion.

Transducer assemblies constructed according to the teachings of this invention may then be provided with mechanical means such as suction cups for attachment to the surface of the transilluminated display. The suction cup is preferably provided with a hinge so that the transducer may be temporarily moved out of the path of observation. In this way, the user of the system may assure that the photocell is placed precisely over the area to be measured.

This invention possesses many other advantages, and has other purposes which may be made more clearly apparent from a consideration of forms in which it may be embodied. These forms are shown in the drawings accompanying and forming part of the present specification. They will now be described in detail, for the purpose of illustrating the general principles of the invention; but it is to be understood that such detailed descriptions are not to be taken in a limiting sense.

BRIEF DESCRIPTION OF THE DRAWINGS

Figure 1:
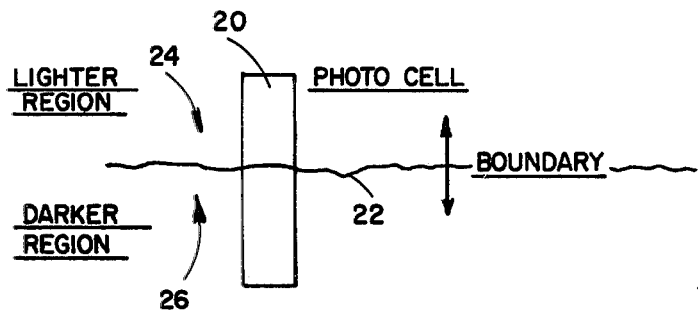
Figure 2:
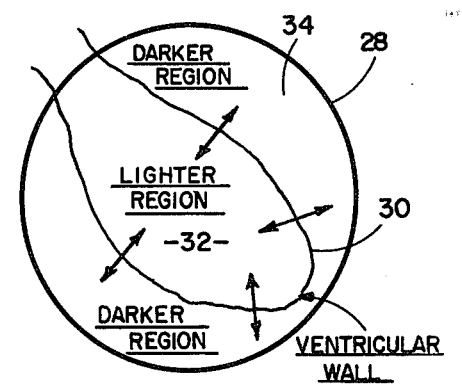
Figure 4:
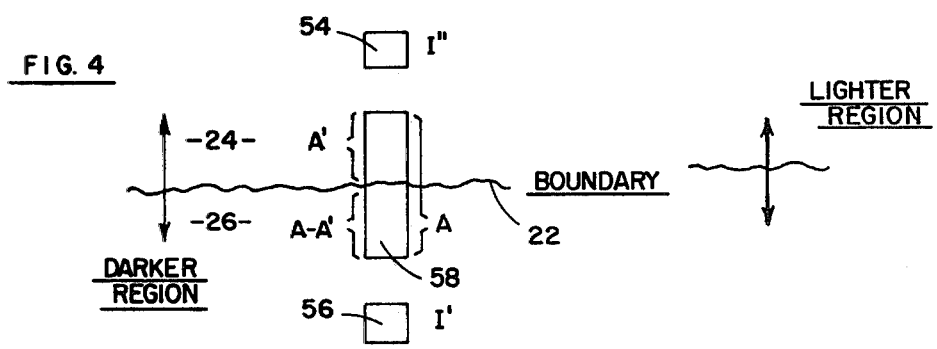
Figure 3:
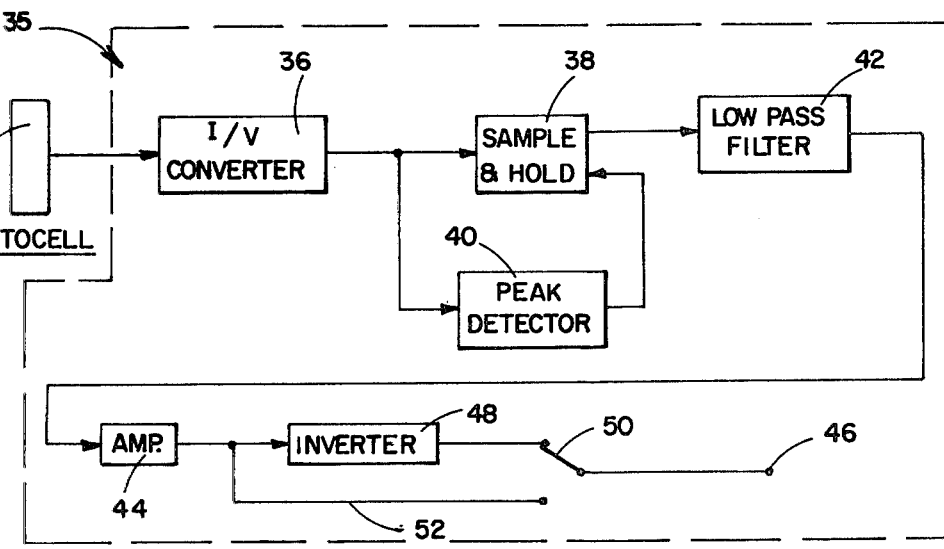
Figure 13:
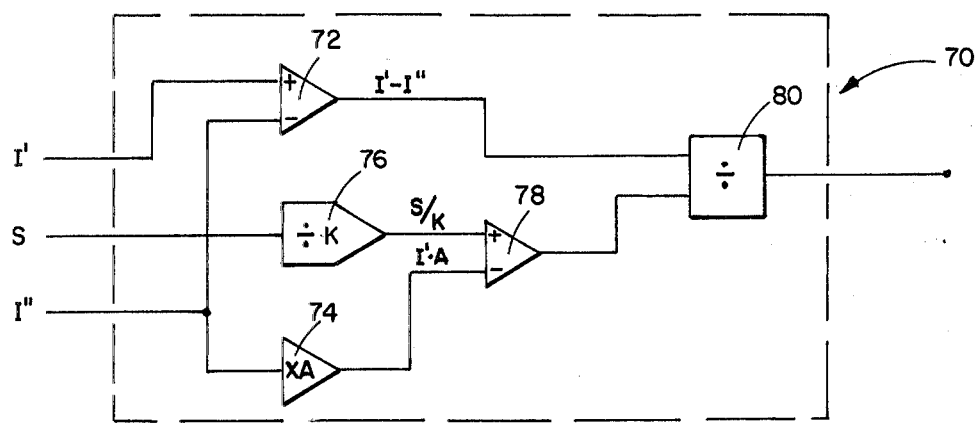
Figure 17A:
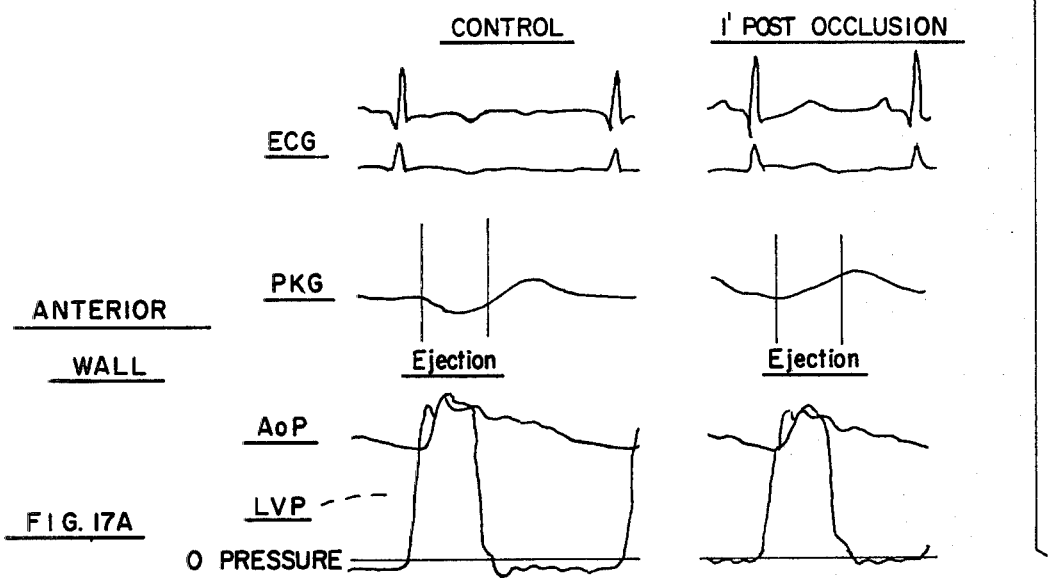
Figure 17B:
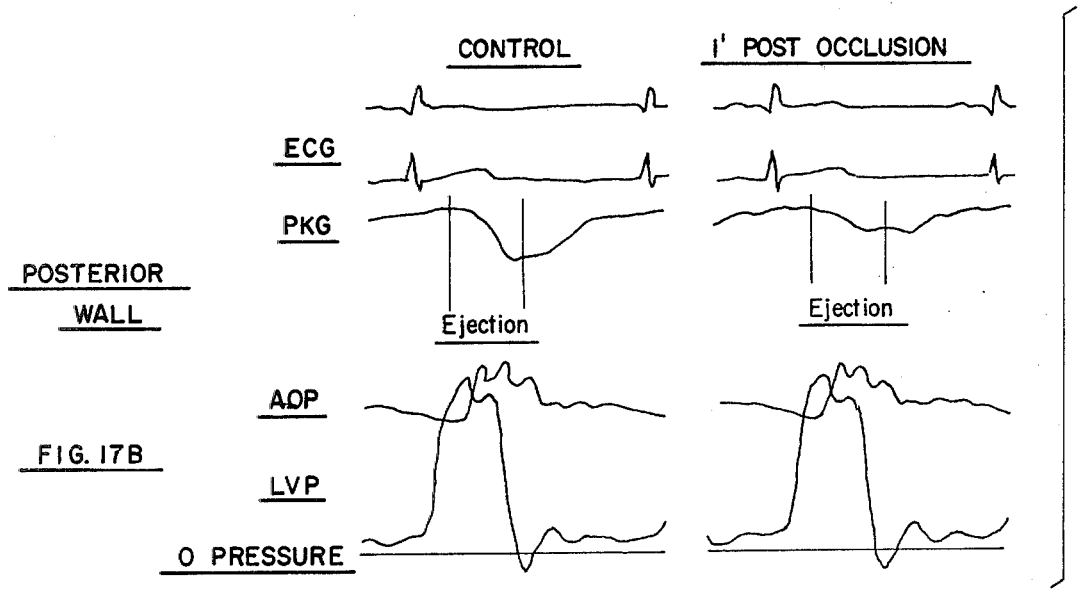
Figure 14:
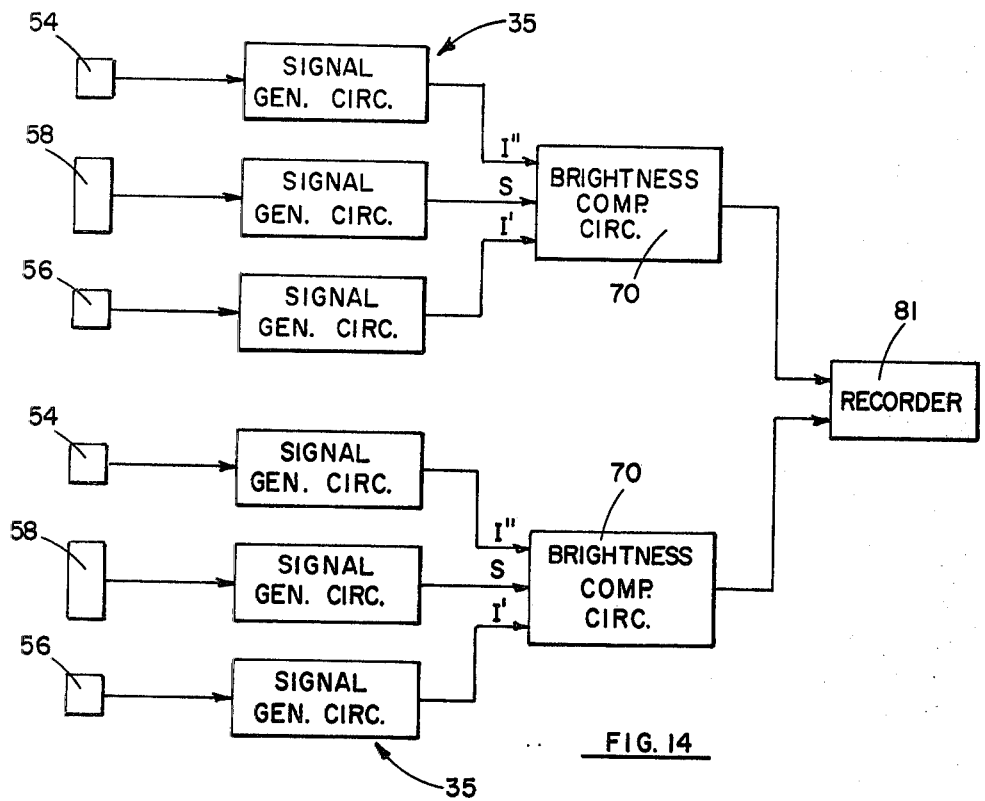
Figure 16:
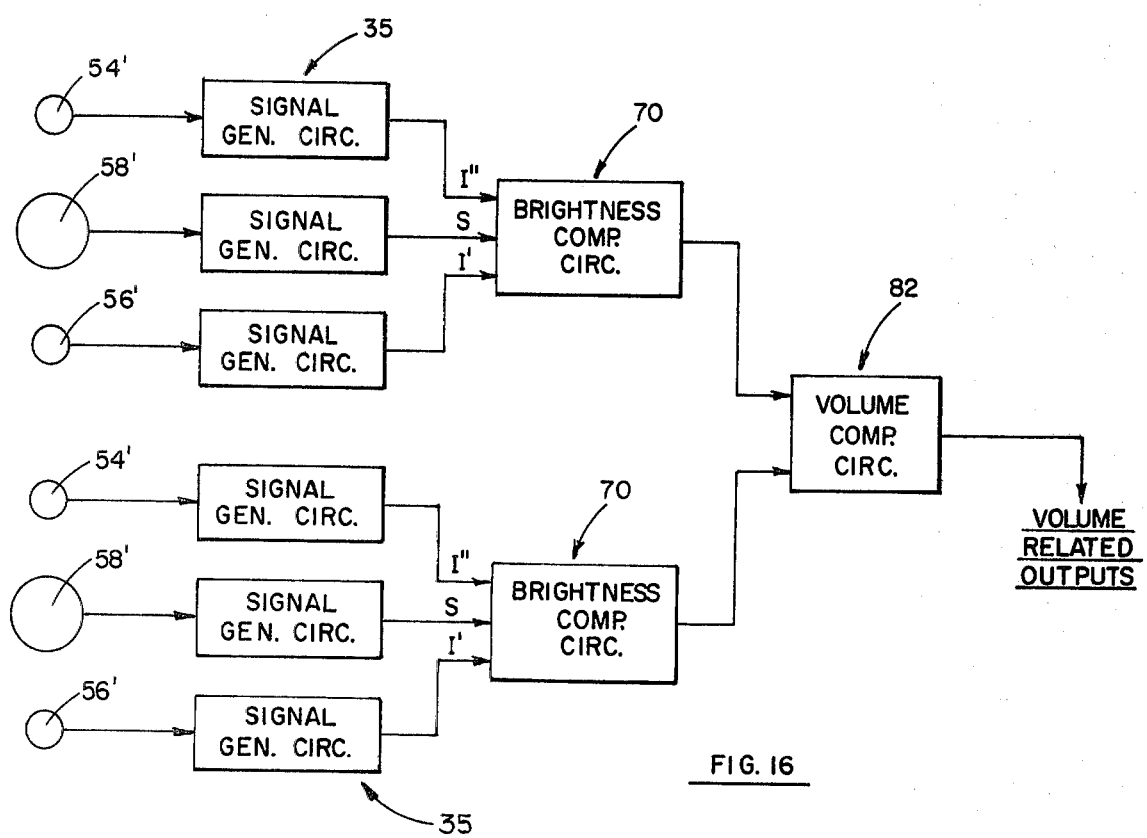

Having thus described the invention in general terms, reference will now be made to the accompanying drawings in which:

FIG. 1 is a schematic illustration of a technique for obtaining linear measurement by means of a phototransducer assembly of the present invention;

FIG. 2 is a schematic illustration of a ventricular wall structure showing light and dark regions for which planimetric measurement may be made by means of a phototransducer assembly of the present invention;

FIG. 3 is a block diagram of a circuit for providing linear measurements from a pictorial source and generating an electrical output signal suitable for recordation by conventional strip chart recorder means;

FIG. 4 is a schematic illustration of the relative positioning of a detecting photocell and reference photocells;

FIG. 5 is a schematic illustration of a detecting photocell and reference photocells in a planimetric measurement;

FIG. 6 is a side elevational view, partially broken away and in section, of a complete transducer assembly to measure linear motion;

FIG. 7 is a top plan view of the transducer assembly of FIG. 6;

FIG. 8 is a bottom view taken substantially along line 8—8 of FIG. 6;

FIG. 9 is a composite top plan view of a detecting photocell transducer assembly and separate reference photocell transducer assemblies;

FIG. 10 is a top plan view, similar to FIG. 7, and showing a phototransducer assembly used for making planimetric measurements;

FIG. 11 is a bottom view of the assembly of FIG. 10;

FIG. 12 is a side elevational view partially in section showing a modified transducer assembly to measure planimetric motion;

FIG. 13 is a block diagram of the computational circuitry to provide a measurement compensated for image changes;

FIG. 14 is a block diagram of the computational circuitry to provide a planimetric measurement compensated for image changes;

FIG. 15 is a schematic block diagram of an analog computation circuit to provide signals representative of various volume related cardiac parameters from two area measurements;

FIG. 16 is a schematic block diagram showing a complete circuit arrangement for producing the various volume related cardiac parameters using the circuit of FIG. 14; and FIGS. 17A and 17B are schematic illustrations showing anterior and posterior cardiac wall functions using two linear photokymograph measurements of the present invention.

DETAILED DESCRIPTION OF PREFERRED EMBODIMENTS

Referring now in more detail and by reference characters to the drawings which illustrate practical embodiments of the present invention, FIG. 1 illustrates the use of a photocell 20 for making linear measurements of a moving boundary 22. In this case, a generally rectangular photocell 20 is placed over an image having the moving boundary 22 which is capable of shifting back and forth between and thereby permitting exposure of greater and lesser portion of a lighter region 24 and a darker region 26 to the photocell 20. Thus, motion of the boundary 22 along the length of the photocell 20 will effectively change the areas which are illuminated by the lighter region 24 and the darker region 26, and, consequently, the integrated average light value over the surface of the entire photocell 20. This change of total luminous energy reaching the photocell surface will produce a linear electrical current analog of the aforesaid change of position of the boundary 22 across the surface of the photocell 20.

For the purpose of making linear measurements, generally rectangularly shaped photocells may be employed. The exact shape of the photocell is not critical, although it should be generally thin in the transverse dimension, that is the dimension perpendicular to the direction of movement, since wide area measurements are not necessarily desired for linear analog representations of the boundary movement.

FIG. 2 illustrates the making of planimetric measurements. In this case, a large round photocell 28 is placed over a portion of the image of a ventricular wall 30 with a lighter region 32 corresponding to the internal space of the ventricle and a darker surrounding region 34 corresponding to the tissue of the ventricular wall and the intraventricular septum. The cardiac cycle progresses from diastole, at which point the lighter region 32 will be at its largest total area, through end systole, at which point the lighter region 32 will be at its smallest. The area of light and the ratio of light to dark detected by the photocell 28 will be an exact analog of the motion of the ventricular wall. This motion of the ventricular wall will produce an output current which is a fairly accurate planimetric measure of the change of area of the lighter region versus the darker region beneath the surface of the photocell 28.

For the purpose of making planimetric measurements, generally round photocells may be employed. Here, again, the exact shape of the photocell is not critical, although the photocell should be sufficiently large so as to cover the desired region being measured. Moreover, a plurality of photocells may be employed for making planimetric measurements, whether or not calibrated. In this way, various measurements can be made simultaneously over the region of interest to form a composite image thereof.

Silicon photocells have several unique properties which make them the preferred choice of photocells in the photokymograph system. The silicon photocells are available in a wide range of sizes and shapes, have good sensitivity and have a linear output over a wide range of luminous flux intensity. Moreover, the silicon photocells are sensitive to a wide range of spectral energy, are rugged and inexpensive. Due to their substantially planar construction, the silicon photocells can be placed directly upon a transilluminated image and provide an electrical output which is a direct linear analog of the integrated light area beneath the cell without any intervening optical mechanism. Further, the electrical output can be generated with almost no inherent delay.

FIG. 3 illustrates a block diagram of an analog signal generating circuit 35 used to make the linear measurements. The signal derived from a photocell, as for example, the photocell 20, is applied as a current to the summing node of a conventional integrated circuit current-to-voltage converter 36. The converter 36 will produce a voltage which is a fairly exact analog of the linear motion of the boundary being measured by the photocell 20. This photocell current produced voltage at the output of the converter 36 will be applied to a sample and hold circuit 38, preferably an integrated circuit amplifier, of conventional design.

The sample and hold circuit 38 is controlled by the action of a peak detector 40, also of conventional design. Thus, when the video image or the cinema image beneath the photocell 20 reaches its greatest instantaneous brightness, a sample of the instantaneous amplitude at that point in time will be selected by the sample and hold circuit 38 under control of the peak detector 40. This sample of the instantaneous amplitude will be held until a subsequent peak is reached, at which point this sample will be replaced by a new sample in the sample and hold circuit 38.

The output of the sample and hold circuit 38 will generally include a series of DC voltage levels corresponding to the instantaneous linear position of the light-dark boundary detected by the photocell 20. The output of the circuit 38 is then applied to the low-pass filter 42 which is a conventional active filter of at least four poles with a typical cut-off frequency of 20 hertz at the -31 3 db point, or in the case of use with cinema image, to 10 hertz. The filter 42 will substantially extract the flicker artifact caused by the nature of the programmatic source being examined. The output from the low-pass filter 42 will be amplified by conventional integrated circuit amplifier 44 to provide amplitude and impedance adjustment for proper interface with conventional chart recording equipment.

The output of the amplifier 44 can be routed to an output terminal 46 of the circuit 35 by one of two routes. The first route includes an inverter 48 having its output connected to a two-position switch 50, which is, in turn, connected to the output terminal 46. The other route comprises a direct connection 52 to the switch 50, the latter of which serves as a polarity selection switch. The switch 50 in the first position, as illustrated in FIG. 3, can provide the output inverted in polarity or, conversely, if the switch 50 is in the second or lower position, the output of the amplifier 44 will be applied directly to the system output terminal 46 and the signal will thus be uninverted.

The inverter 48 along with the polarity selection switch 50 constitute a polarity selector. This is desirable inasmuch as many images can be relatively black on white or otherwise relatively white on black. In a cine source, the left ventricle is usually whiter than the background, whereas in videofluoroscopy, the ventricle is usually darker than the background. Thus, the polarity selector may be used to provide compatible data, notwithstanding the type of image.

It is also possible to employ a plurality of simultaneously operated transducer assemblies of the present invention in order to compare motion of one part of the structure relative to motions of other parts of the structure. Thus, for example, a plurality of photocells, such as the photocells 20, could be placed at various positions along the cardiac wall or a series of sequential images of the cardiac wall in movement. In this way, measurement of movement of one part of the cardiac wall could be simultaneously made relative to movement of other parts of the cardiac wall. It should be understood that each of the individual photocells would be used in conjunction with each of an individual analog computation circuit 35 in order to provide the electrical analog outputs representative of the movements of the various portions of the cardiac wall.

In order to provide a compensation for changes of overall brightness or contrast ratio of the image being examined in a linear measurement, two reference photocells, 54 and 56, may be employed as illustrated in FIG. 4. The reference photocell 54 and reference photocell 56 are located in conjunction with a detecting or measuring photocell 58, substantially similar to the photocell 20. The reference photocell 54 will be continuously illuminated at a level determined by the average brightness of a lighter region, e.g. the lighter region 24, and the reference photocell 56 will be continuously illuminated by the average intensity of a darker region, e.g. the darker region 26, separated by a movable boundary, e.g. the boundary 22.

FIG. 5 illustrates an arrangement in which brightness levels and contrast between a light and dark region may be compensated in area measurements. In this case, a detecting photocell 58' of generally circular shape is placed over an object H in which area measurement is to be made. The object H may have a surface area h in the plane to be measured and may represent, for example, the dark region. The object H, which may represent a heart, for example, is located in a larger region R representing, e.g., a light region and which has a surface area r. The photocell 58' is generally larger than the total surface area in one plane being measured than the object H. The area of the object H is defined by the periphery of the object, which represents a boundary, in the plane to be measured.

One reference photocell 54' is located in the region R beyond the object H. The other of the reference photocells is located within the measuring photocell 58' and lies over the darker region, i.e., the object H. In this way, compensation may be made for the variations in light impinging on the measuring photocell 58' and the contrast between the two regions R and the object H.

The surface area of the measuring photocell 58' and the surface areas of the reference photocells 54' and 56' are known or easily determined. The measuring photocell 58' may have a surface area x, the reference photocell 54' may have a surface area y, and the reference photocell 56' may have a surface area z which are known. The object H has area H as indicated above and the objective is to determine this area H. The brightness of the object H is determined by reference photocell 56', this brightness being proportional to the output of photocell 56' divided by its area Z. Similarly, the brightness of region R can be determined by dividing the output of the reference photocell 54'. This situation is directly analogous to the linear transducer described above, and the same equations and circuitry are applicable to the linear and planar cases.

FIGS. 6–8 illustrate the mechanical construction of one transducer assembly 57 embodying the reference photocells 54 and 56, and a signal measuring photocell 58 substantially similar to the photocell 20. The measuring photocell 58 may be mounted on the lower relatively flat surface of a retainer block 60. The first of the reference photocells 54 may be mounted on the retainer block 60 beyond one of the transverse ends of the cell 58. The other reference photocell 56 may be mounted on the retainer lock 60 beyond the opposite transverse end of the cell 58, in the manner as illustrated in FIGS. 7 and 8 of the drawings. In this way, one of the reference photocells will be located over the lighter region when the other of the reference photocells is located over the darker region and vice versa. If desired, the photocells may be slightly recessed from the lower surface thereof in the manner as illustrated in FIG. 6 of the drawings.

The retainer block 60 can be hinged by being mounted to a support plate 62 through a hinge connection 64 as illustrated in FIGS. 6 and 7 of the drawings. Further, the support plate 62 is provided with one or more suction cups 66 connected to the plate 62 by means of a depending leg 68. In this way, it is possible to lift the retainer block 60 and the photocells carried thereby away from the line of sight of the user. This construction also permits the transducer to be placed over any area of the image to be examined and measured at the will of the operator. Moreover, by hingedly mounting the photocell transducer assembly and locating same in slightly spaced relation to the surface of the displayed image, it is possible to observe the displayed image without making measurements and to assure that the transducer is properly positioned over that portion of the image which is to be measured for providing the output data signal.

FIG. 9 illustrates a modified form of transducer assembly 57a of the present invention in which the measuring photocell 58 is mounted in one retaining plate 60a connected to a support plate 60a provided with suction cups 66a, similar to the transducer assembly 57. One of the reference photocells 54 may be mounted in a retaining plate 60b which is, in turn, connected to a support plate 62b, again provided with suction cups 66b, similar to the transducer assembly 57. Finally, the second of the reference photocells 56 may be mounted in a retaining plate 60c which is, in turn, connected to a support plate 62c also provided with suction cups 66c similar to the transducer assembly 57.

The construction of FIG. 9 permits the reference photocells to be placed at generally any desirable location to detect the levels of light from the light and the dark regions. Thus, light and dark regions similar to the area under the measuring or detecting photocell 58 may exist elsewhere on the structure, or the series of sequential images of the structure. Accordingly, the reference photocells 54 and 56 may be located over the light and dark regions at such other location beyond the region over which the measuring photocell is located.

FIGS. 10 and 11 illustrate the mechanical construction of a transducer assembly 57' embodying circular reference photocells 54' and 56', and a large area circularly shaped signal measuring photocell 58' substantially similar to the photocell 22. This transducer assembly 57' embodies those photocells used in making area measurements. The reference photocell 54' and the measuring photocell 58' are mounted on one relatively flat surface of a retainer block 60d and may be slightly recessed from the surface thereof, in the same manner as the cells 54 and 58 were mounted in the retainer block 60 of the transducer assembly 57. The second reference photocell 56' is embedded in an aperture located within the measuring photocell 58', preferably somewhat centrally thereof. Again, the lower surface of the reference photocell 56' may be generally flush with the lower surface of the photocell 58'.

The retainer block 60d can be hinged by being mounted to a support plate 62d through a hinged connection 64d as illustrated in FIGS. 10 and 11 of the drawings. Further, the support plate 62d is provided with one or more suction cups 66d connected to the plate 62d by means of a depending leg (not shown) similar to the assembly 57. This construction also permits the transducer to be placed over any area of the image to be examined and measured at the will of the operator and affords the same advantages as the photocell transducer assembly 57.

FIG. 12 illustrates another embodiment of the photocell transducer assembly in which one of the reference photocells 54' is embedded in the measuring photocell 58'. This measuring photocell is, in turn, secured to the lower flat surface of a retaining plate 60e secured to a support plate provided with suction cups (not shown) similar to the construction of the assembly 57. The other of the reference photocells 56 is similarly mounted on a separate retaining plate 60e again secured to a support plate with suction cups (not shown), similar to the transducer assembly 57. This latter form of transducer assembly also affords the added advantage of locating at least one of the reference photocells over another location of the structure or the series of sequential images thereof.

FIG. 13 is illustrative of analog computational brightness compensating circuit 70, as shown in block diagram form, to provide an output of a linear measurement or a planimetric measurement compensated for changes in brightness or image intensity. The output from the reference photocell 56, designated as I', is applied to the non-inverting input of a summing amplifier 72 of conventional design. The output of the second reference photocell 54, designated as I'', and which is located over the other region of the image, is applied to the inverting input of the subtractor connected to operational summing amplifier 72. This latter output I'' is also applied to a conventional analog operational amplifier 74. The output of the measuring photocell 58, designated as S, is applied to a conventional operational amplifier 76 serving as a scaling amplifier. By means of a suitable resistive feedback in the amplifier 74, the reference signal from the photocell 56 is amplified to provide a base reference value for computation. This base reference value is applied to the inverting input of an operational amplifier 78. The signal S derived from the photocell 58 measuring the motion of the light-dark boundary is amplified and, in effect, scaled by the factor K in the conventional operational amplifier 76 to compensate for the characteristics of the photocell 58 and image size change due to X-ray or optical image projection induced errors and provide a properly scaled output signal for recordation. The output of this scaling amplifier 76 is then applied to the noninverting input of the summing operational amplifier 78.

The output of the summing amplifier 78 represents an analog of the difference between the instantaneous brightness detected by the reference photocell 56 and the integrated area brightness detected by the measuring photocell 58. This signal is then applied to the divisor input of a conventional analog divider module 80, and the previously derived difference signal from the summing amplifier 78 is applied to the dividend input of this analog divider 80. The quotient output of the analog divider 80 will then represent only that portion of the signal derived from the motion of the boundary wall along the length of the measuring photocell 58 with any artifact signal produced by changes in gamma or average scene brightness being measured by the reference photocells 54 and 56 and extracted from the output signal by this computational circuit.

FIG. 14 illustrates the arrangement in which a pair of phototransducer assemblies 57 are used to measure movement in two different portions of a moving structure or a series of sequential images thereof. Each of the transducer assemblies comprise a detecting photocell 58 and reference photocells 54 and 56, as aforesaid. The outputs of each of the cells for one assembly 57 are introduced into individual signal generating circuits 70 and the outputs of cells for the other assembly 57 are introduced into different signal generating circuits. Thus, one circuit 35 is provided for each photocell. The outputs of the signal generating circuits 35 are thereupon introduced into individual brightness compensating circuits 70, where the outputs of the circuits 70 may be displayed on a suitable display device. A recording means 81, in the form of e.g. a chart recorder, may receive the two outputs of the circuits 70. In this way, the two outputs may be recorded simultaneously for comparison. The recording means may adopt the form of a display device. Thus, the outputs of the circuits 70 may be converted to an equivalent digital format for display on a digital display device.

An analog volume computational circuit 82, more fully illustrated in block diagram form in FIG. 15, is provided to perform measurements and derivations from two photokymograph signals in order to generate cardiac volume parameters. Two measurements, A' and A'', which are biplane area measurements determined by the system of the present invention, may be used. These two area measurements A' and A'' are introduced into and multiplied in an analog multiplier 84 and the product is applied to the input of a logrithmic amplifier 86 of conventional design to produce an output electrical analog signal corresponding to the log of the product of the two areas. This output from the amplifier 86 is, in turn, multiplied by a numeric value of, e.g. 0.776, in an operational amplifier 88 having a suitable conventional feedback circuit therein. The output of the amplifier 88 is applied to the non-inverting input of an operational amplifier 90, operated as a subtractor, with the negative input from suitable DC circuit means (not shown) to provide a net numerical electrical analog signal subtraction of e.g. 0.405 from the amplified product previously derived. The output signal from the amplifier 90 will then have a value of 0.776 log (A' A")−0.405. The multiplier may also be selected to compensate for image size relative to original heart size caused by X-ray or optical systems. The output signal from the amplifier 90 is then multiplied by 10 to provide a convenient amplitude output in a conventional operational scaling amplifier 92.

The output of the amplifier 92 will be a continuous analog signal referring to instantaneous ventricular volume as a function of time, designated as V/T in FIG. 15. This output will also be in a form suitable for recordation by a conventional chart recording. A portion of this output signal from the amplifier 92 is sampled by a positive peak detector 94 and a negative peak detector 96. Both peak detectors 94 and 96 are of conventional construction. The positive peak detector 94 provides a measure of end diastolic volume available in electrical analog form and designed as EDV. The negative peak detector 96 by similar means produces a measure of end systolic volume, designated as ESV.

The outputs of the two peak detectors 94 and 96 provide a measure of end diastolic volume and end systolic volume, respectively, as aforesaid. These two outputs from the detectors 94 and 96 may be algebraically summed in a conventional contractor connected operational amplifier 98 to produce a difference signal, designated as SV, which is an analog of the stroke volume as EDV−ESV=SV. The signal representation of stroke volume, in turn, may be applied to a dividend input of an analog divider circuit 100 of conventional construction which also receives the output signal from the positive peak detector 94 representative of end diastolic volume. The divider circuit 100 will produce an output signal, i.e., a quotient which is an electrical analog representative of the resultant ejection fraction, designated as EF. In this way, many of the parameters normally of interest to a cardiologist can be generated, measured and recorded together with the electrocardiogram in real time to produce a permanent diagnostic record of heat motility, activity, wall position, wall position changes, and other diagnostic information for later analysis.

FIG. 16 illustrates an arrangement in which volumetric cardiac parameters may be measured and displayed using the volume computational circuit 82 of FIG. 15. In this case, a first measuring transducer 58' and accompanying reference photocells 54' and 56', and a second measuring transducer 58' and accompanying reference photocells 54' and 56' are employed. The outputs of each of these photocells are introduced into individual signal generating circuits 35. The signal generating circuits 35 for the first set of transducers is introduced into a brightness compensating circuit 70 and the outputs of the signal generating circuits 35 for the second set of transducers are introduced into a second brightness compensating circuit 70.

It can be observed that the output of the reference photocells 56', which are processed in the signal generating circuits 35, constitute an I' input and the outputs of the reference photocells 54', similarly processed, constitute an I" input. The outputs of the measuring photocells 58', which are also processed in the signal generating circuits 35, serve as S inputs to the respective brightness compensating circuits 70.

The outputs of the two brightness compensating circuits are thereupon introduced into a volume computational circuit 82 where the various output parameters can be determined in the manner as previously described. Here, again, it can be observed that the outputs of the circuit 82 could be displayed on a suitable display device.

FIG. 17A illustrates a segment of a strip chart record achieved with the system of the present invention by linear measurements of the anterior wall of the ventricles of a beating heart. The strip chart record of FIG. 17A also illustrates an electrocardiograph signal simultaneously taken with a conventional electrocardiogram, and including the aortic pressure wave form, designated as AoP, and the left ventricular pressure wave form, designated as LVP. Also illustrated are reference values and timing marks associated with these signals for convenience during data reduction.

FIG. 17A also illustrates the zero pressure, designated as "0 pressure". The strip chart recording achieved with the photokymograph of the present invention is also designated as PKG. FIG. 17B illustrates information similar to that of FIG. 17A, but for the posterior wall of the ventricles of the same beating heart. Moreover, in both FIGS. 17A and 17B, plots are shown for a control time frame and for a post occlusion time frame. By further reference to FIGS. 17A and 17B, it can be observed that in the time frame subsequent to the QRS complex of the ECG wave form, the motion of the anterior wall corresponding to the systolic contraction of the ventricle is downward. This causes an increase of aortic pressure as seen in the aortic wave form and is due to the decrease in total internal volume of the ventricle. At the time of diastole, as shown by the negative I wave pulse, corresponding to the relaxation and filling of the ventricles, it can be observed that the anterior wall photokymograph signal derived from the photocell transducer of the present invention is upward corresponding to a net increase in total ventricle volume. Simultaneously, the left ventricular pressure falls sharply as the end of the contraction and the beginning of the relaxation or diastolic phase of this beat is reached.

The aortic pressure also shows a sharp drop at the time of the onset of diastole. This aortic pressure will continue to fall slowly until the onset of the next systolic phase. During the same time frame, the motion of the posterior wall, as shown by the posterior wall photokymogram trace labeled PKG, is in the opposite direction. From the two PKG traces, it is apparent that during the period of systolic contraction of the ventricles, a total net volume reduction of the blood contained within the ventricles is accompanied by a pressure peak within the ventricle and a volume flow peak shown by the pressure wave form of aortic pressure.

Thus, the difference between the two photokymograph signals is then a direct measure of the total change of cardiac wall motion. This total change of cardiac wall motion can be used to derive ventricular volume v, as a function of time, end diastolic volume of the ventricle, end systolic volume of the ventricle, the difference between the two being stroke volume, and stroke volume divided by end diastolic volume providing a measure of ejection fraction, as previously described. These measurements will then provide the physician with the diagnostic data from which he can deduce the patient's cardiovascular system condition and prescribe any indicated treatment.

In accordance with the above, it can be observed that the photokymograph of the present invention is highly effective in obtaining both qualitative and quantitative records of various forms of dynamic movement. Particularly, the photokymograph is highly effective in obtaining both qualitative and quantitative records of cardiac movements including segmental ventricular wall motion, hemodynamic parameters, and the like. Moreover, the photokymograph is applicable to generally any system producing a moving image and particularly a cardiac image. In addition, it can be observed that the photokymograph can produce moving images of cardiac tissue and related tissue, and is also able to detect and measure the linear motion of cardiac valves. Moreover, cardiac cycle time information can be acquired from aortic pulsation.

The photokymograph is generally capable of use with all forms of imaging and operates on a visual image itself. Moreover, the system of the present invention provides a means for tracking and quantifying structural movements at any desired location on the image and in any desired orientation.

By virtue of the construction of the system of the present invention, the photocell transducer can be placed at any desired position on the image and in any desired orientation. Multiple simultaneous data records can be readily obtained with this system. For example, simultaneous segmental wall motion data can be obtained from various positions along the ventricular wall, simultaneous biplane ventricular area can be measured and aortic root pulsation or valve motion can also be detected. One of the unique aspects of the present invention is that the image changes can be quantified in a simple reliable and inexpensive way.

The photokymograph of the present invention eliminates generally all artifact caused by flickering nature of images. In addition, compensation for image intensity variation and for contrast medium wash-out is provided. Through the use of the multiple simultaneous transducers, it is possible to measure segmental ventricular wall motion.

Thus, there has been illustrated and described a unique and novel apparatus and method for image analysis of dynamic motion and which therefore fulfills all of the objects and advantages sought therefore. It should be understood that many changes, modifications, variations and other uses and applications will become apparent to those skilled in the art after considering this specification and the accompanying drawings. Therefore, any and all such changes, modifications, variations, and other uses and applications which do not depart from the spirit and scope of the invention are deemed to be covered by the invention which is limited only by the following claims.

Having thus described our invention, what we desire to claim and secure by Letters Patent is:

1. A system for detecting and measuring the linear motion in at least one dimension of a portion of either a dynamically movable structure or visual image representations of that structure and providing an analog signal representative of the movement, said system comprising:

(a) sensing means for detecting amd measuring the light change pursuant to a moving boundary on the structure or a series of sequential image representations of that structure moving between dark and light regions on said dynamically movable structure or on said series of sequential visual image representations of said dynamically movable structure, and which sequential visual image representations are displayed in sequence at a rate to represent the movable structure during movement thereof, said sensing means generating a current signal representative of the boundary movement, (b) conversion means for receiving the current signal from said sensing means for generating an analog voltage signal as a fairly exact analog of the current signal and being representative of and directly related to the amount of movement of said boundary on the dynamically movable structure or on the series of sequential visual image representations, (c) selection means operatively connected to said conversion means for selecting a sample of predetermined instantaneous amplitude and at least temporarily holding such sample, (d) detection means operatively connected to said selection means for aiding in and determining a sample of predetermined instantaneous amplitude to thereby determine a maximum limit of movement of the boundary at least in one region, and (e) means operatively connected to at least said selection means for providing a representation of the amount of movement of said boundary.

2. The system of claim 1 further characterized in that said sensing means comprises a photocell.

3. The system of claim 1 further characterized in that said sensing means comprises an elongate main sensing photocell having an area of movement in the direction of greatest length generally parallel to the direction of movement of the boundary.

4. The system of claim 3 further characterized in that the system comprises means for compensating for image intensity variation.

5. The system of claim 4 further characterized in that the means for compensating comprises at least two reference photocells.

6. The system of claim 3 further characterized in that said main sensing photocell is mounted on a shiftable member enabling shiftable movement of same.

7. The system of claim 1 further characterized in that said movable structure is a body tissue and the analog signal is representative of and linearly related to the movement of the body tissue.

8. The system of claim 7 further characterized in that the body tissue is cardiac tissue or cardiovascular tissue.

9. The system of claim 1 further characterized in that said structure or images present a region in which a measurement is to be made, and said sensing means comprises a photocell having an area at least as large as said region on said structure or images thereof to be measured to provide a planimetric measurement.

10. A method for detecting and measuring the linear motion in at least one dimension of a dynamically movable structure or visual image representations of that structure and providing an analog signal representative of the amount of movement, said method comprising:

(a) detecting and measuring a light change pursuant to a moving boundary on the movable structure or series of sequential visual image representations of that structure moving between dark and light regions on said dynamically movable structure or on said series of sequential visual image representations of said dynamically movable structure and generating a detecting current signal thereby, and which sequential visual image representations are displayed in sequence at a rate to represent the movable structure during movement thereof, (b) generating an analog voltage signal in response to the detecting current signal and as a fairly exact analog of the current signal and being representative of and directly related to the amount of movement of said boundary on the dynamically movable structure or on each of the series of sequential visual image representation, (c) selecting a sample of predetermined instantaneous amplitude and at least temporarily holding such sample, (d) holding the selected sample until another sample of higher predetermined instantaneous amplitude is detected to thereby determine a maximum limit of movement of the boundary at least in one region, and (e) providing a representation of the amount of movement.

11. The method of claim 10 further characterized in that the method comprises detecting a signal which has highest instantaneous amplitude.

12. The method of claim 11 further characterized in that the method comprises compensating for image intensity variation.

13. The method of claim 12 further characterized in that said method comprises compensating for image intensity variation with at least two reference photocells.

14. The method of claim 10 further characterized in that said movable structure is a body tissue and the analog signal is representative of and directly related to the movement of the body tissue.

15. The method of claim 14 further characterized in that the body tissue is cardiac tissue or cardiovascular tissue.

16. The method of claim 10 further characterized in that said movable structure is a body tissue and the analog signal is representative of area changes in the body tissue.

17. The method of claim 16 further characterized in that the body tissue is cardiac tissue or cardiovascular tissue.

18. A system for detecting and measuring the motion of a dynamically moving structure having a boundary moving between light and dark areas, said system comprising:

(a) means for detecting and measuring the light changes in response to a boundary on either said structure or a series of sequential image representations of that structure moving between adjacent dark and light areas on said dynamically moving structure or said series of sequential visual image representations of said structure, said last named means generating a current representing signal therefrom which is an analog of the motion of the boundary, (b) sampling means for sampling an instantaneous amplitude of the signal representing a greatest instantaneous brightness, (c) conversion means for converting the current representing signal to a voltage equivalent signal, (d) peak detection means operatively connected to said sampling means and enabling said sampling means to hold the signal of highest amplitude thus sampled until an instantaneous amplitude of greater brightness is detected, and using the instantaneous amplitude of greatest brightness to determine maximum limit of movement of the boundary, (e) filter means operatively connected to said sampling means for extracting flicker artifact from the signal to thereby provide an analog signal representative of the motion of the boundary, and (f) means to receive the analog signal and provide a representation of the amount of movement based on the analog signal.

19. The system of claim 18 further characterized in that the output of said sampling means is controlled by a means forming part of said peak detection means.

20. The system of claim 19 further characterized in that said system comprises an amplifier and the output of said filter means is introduced into said amplifier for amplitude and impedance adjustment of the signal.

21. The system of claim 18 further characterized in that the means for detecting and measuring the light changes comprises sensing means for detecting the change of light as said boundary moves between dark and light regions on a series of sequential visual image representations of a dynamically movable structure, and where said sequential visual image representations are displayed in sequence at a rate to represent the movable structure during movement thereof.

22. The system of claim 18 further characterized in that the system comprises at least two photocell means for compensating for image intensity variation.

23. The system of claim 18 further characterized in that said movable structure is a body tissue and the analog signal is representative of area change of the body tissue.

24. The system of claim 23 further characterized in that the body tissue is cardiac tissue or cardiovascular tissue.

25. A method for detecting and measuring the motion of a dynamically moving structure, said method comprising:

(a) detecting and measuring light changes in response to a boundary on said structure or a series of sequential image representations of that structure moving between two adjacent dark and light areas, (b) generating an electrical signal from the detected changes in levels of light which is an analog of the motion of the boundary, (c) sampling an instantaneous amplitude of the signal which represents a greatest instantaneous brightness, (d) holding the amplitude thus sampled until an instantaneous amplitude of greater brightness is sampled and detected, (e) extracting flicker artifact from the signal to thereby provide an analog signal relatively free of flicker artifact representative of the motion of the boundary, and (f) providing a representation of the motion of the boundary based on said analog signal.

26. The method of claim 25 further characterized in that said method comprises adjusting for amplitude and impedance of the signal.

27. The method of claim 25 further characterized in that the step of detecting and measuring the light changes comprises detecting the changes of light as said boundary moves between dark and light regions on a series of sequential visual image representations of a dynamically movable structure, and which sequential visual image representations are displayed in sequence at a rate to represent the movable structure during movement thereof.

28. A system for measuring a biplane cross-sectional area of a portion of a dynamically movable structure, said system comprising:
(a) first photocell means for detecting and measuring the change in amount of light in response to a movable boundary at a first location on said structure moving between adjacent light and dark areas on said movable structure, said first photocell means having an active surface area which is sufficiently large enough to effectively cover that portion of the structure which is being examined for area change,
(b) means for generating an analog signal representative of and related to the light changes to determine a biplane cross-sectional area in that portion of the structure including said first location, and
(c) means for receiving the analog signal and representing the measurement of the biplane cross-sectional area based on the analog signal.

29. The system of claim 28 further characterized in that said system measures volume parameters of said movable structure, said system further comprising second photocell means for simultaneously detecting and measuring the change in amount of light in response to a movable boundary at a second location on said structure moving between dark and light areas on said movable structure, said second photocell means also having an active surface area which is sufficiently large enough to effectively cover that portion of the structure which is being examined for area change, means generating a second analog signal from the second means for detecting and measuring, and means for computing a measurement of the volume parameters from said first and second analog signals.

30. The system of claim 29 further characterized in that the means for detecting and measuring the levels of light detects and measures the changes of light as the movable boundaries move between dark and light regions on a series of sequential visual image representations of a dynamically movable structure, and which visual image representations are displayed in sequence at a rate to represent the movable structure during movement thereof.

31. The system of claim 28 further characterized in that said system comprises:
(a) sampling means for sampling an instantaneous amplitude of the signal which represents greatest instantaneous brightness,
(b) peak detection means operatively connected to said sampling means for detecting a sample having an instantaneous amplitude of greatest brightness and enabling said sampling means to hold the amplitude thus detected until an instantaneous amplitude of greater brightness is sampled and detected, and
(c) filter means operatively connected to said sampling means for extracting flicker from the signal to thereby provide an analog signal representative of the biplane cross-sectional area.

32. The system of claim 28 further characterized in that said movable structure is a body tissue and the analog signal is representative of and related to the area of movement of the body tissue.

33. The system of claim 32 further characterized in that the body tissue is cardiac tissue or cardiovascular tissue.

34. The method of claim 33 further characterized in that the steps of detecting and measuring the levels of light comprises detecting and measuring the changes of light as the movable boundaries move between dark and light regions on a series of sequential visual image representations of a dynamically movable structure, and which sequential visual image representations are displayed in sequence at a rate to represent the movable structure during movement thereof.

35. A method for measuring a biplane cross-sectional area of a portion of a dynamically movable structure, said method comprising:
(a) locating a first photocell over that portion of the dynamically movable structure in which area measurement is to be made, said first photocell having an active surface area which is sufficiently large enough to cover that portion of the structure which is examined for area change,
(b) detecting and measuring the change in amount of light with said first photocell in response to a movable boundary at a first location on said movable structure moving between adjacent light and dark areas on said structure,
(c) generating an analog signal representative of and related to the light changes at said location,
(d) processing said signal to determine a biplane cross-sectional area in that portion of the structure including said first location, and
(e) representing the measurement of the biplane cross-sectional area based on the processed signal.

36. The method of claim 35 further characterized in that said method comprises measuring volume parameters of said movable structure, said method further comprising locating a second photocell over a portion of the dynamically movable structure at a second location thereon and over a second area in which a measurement is to be made, said second photocell also having an active surface area which is sufficiently large enough to cover the second area which is to be examined, detecting and measuring the change in amount of light in response to a movable boundary at said second location on said movable structure moving between adjacent light and dark areas on said structure, with said second photocell generating a second analog signal from the second means for detecting and measuring, and computing volume parameters from said first and second analog signals.

37. The method of claim 36 further characterized in that said movable structure is a body tissue and the analog signal is representative of and related to the movement of the body tissue.

38. The method of claim 35 further characterized in that said method comprises:
(a) sampling an instantaneous amplitude of the signal which represents greatest instantaneous brightness,
(b) holding the amplitudes thus sampled until an instantaneous amplitude of greater brightness is detected, and
(c) extracting flicker from the signals to thereby provide an analog signal relatively free of flicker representative of the biplane cross-sectional area.

39. The method of claim 37 further characterized in that the body tissue is cardiac tissue or cardiovascular tissue.

40. A system for detecting and measuring the motion representing area change of dynamically moving body tissue, said system comprising:

(a) means for detecting and measuring the light changes in response to a boundary on either said body tissue or series of sequential image representations of that same body tissue moving between adjacent dark and light areas on said dynamically moving body tissue or said series of sequential visual image representations of said body tissue, said last-named means generating an electrical signal therefrom which is an analog of the motion of the boundary, (b) sampling means for sampling an instantaneous amplitude of the signal representing a greatest instantaneous brightness, (c) peak detection means operatively connected to said sampling means and enabling said sampling means to hold the amplitude thus sampled until an instantaneous amplitude of greater brightness is detected, (d) filter means operatively connected to said sampling means for extracting flicker artifact from the signal to thereby provide an analog signal representative of the motion of the boundary and thereby representative of area change, and (e) means to receive the analog signal and provide a representation of the amount of area change based on said analog signal.

41. The system of claim 40 further characterized in that the output of said sampling means is controlled by a means forming part of said peak detection means.

42. The system of claim 41 further characterized in that said system comprises an amplifier and the output of said filter means is introduced into said amplifier for amplitude and impedance adjustment of the signal.

43. The system of claim 41 further characterized in that said signal from the means for detecting is a current representative signal and a converter is interposed between the means for detecting and the sampling means for converting the signal to a voltage equivalent thereof.

44. The system of claim 40 further characterized in that the means for detecting and measuring the light changes comprises sensing means for detecting the change of light as said boundary moves between dark and light regions on a series of sequential visual image representations of a dynamically movable body tissue and where said sequential visual image representations are displayed in sequence at a rate to represent the movable body tissue during movement thereof.

45. The system of claim 40 further characterized in that the system comprises at least two photocell means for compensating for image intensity variation.

46. The system of claim 40 further characterized in that the body tissue is cardiac tissue or cardiovascular tissue.

47. A system for detecting and making a planimetric measurement of area change motion in at least one portion of either a dynamically movable structure or visual image representations of that structure and providing an analog signal representative of the movement, said system comprising:

(a) a photocell for detecting and measuring the light change pursuant to a moving boundary on the structure of a series of sequential image representations of that structure moving between dark and light regions on said dynamically movable structure or on said series of sequential visual image representations of said dynamically movable structure, and which sequential visual image representations are displayed in sequence at a rate to represent the movable structure during movement thereof, said photocell having an active surface area which is sufficiently large enough to effectively cover that portion of the structure or visual image representations which is examined for area change and generating a signal representative of the boundary movement, (b) means for receiving the signal from said sensing means for generating an analog signal representative of and directly related to the amount of movement of said boundary on the dynamically movable structure or on the series of sequential visual image representations, and (c) means operatively connected to at least said selection means for providing a representation of the measurement of area change.

48. The system of claim 47 further characterized in that said sensing means comprises a photocell.

49. The system of claim 48 further characterized in that the signal from said sensing means is a current representative signal and said means for generating an analog signal converts the current representative signal to a proportional voltage representative signal.

50. The system of claim 49 further characterized in that the system comprises means for compensating for image intensity variation.

51. The system of claim 50 further characterized in that the means for compensating comprises at least a pair of reference photocells.

52. The system of claim 50 further characterized in that said movable structure is a body tissue and the analog signal is representative of and linearly related to the movement of the body tissue.

53. The system of claim 52 further characterized in that the body tissue is cardiac tissue or cardiovascular tissue.

54. A method for detecting and measuring the motion of a dynamically moving structure, said method comprising:

(a) locating a first photocell over a first portion of the structure or series of image representations in which an area measurement is to be made, said first photocell having an active surface area which is sufficiently large enough to effectively cover that portion of the structure or the portion of the series of visual image representations which is being examined for area change, (b) detecting and measuring light changes in response to a boundary on said structure or a series of sequential image representations of that structure between two adjacent dark and light areas, (c) generating an electrical signal from the detected changes in levels of light which is an analog of the motion of the boundary, (d) sampling an instantaneous amplitude of the signal which represents a greatest instantaneous brightness, (e) holding the amplitude thus sampled until an instantaneous amplitude of greater brightness is sampled and detected, (f) extracting flicker artifact from the signal to thereby provide an analog signal relatively free of flicker artifact representative of the motion of the boundary, and (g) providing a representation of the motion of the boundary based on said analog signal.

55. The method of claim 54 further characterized in that said method comprises adjusting for amplitude and impedance of the signal.

56. The method of claim 55 further characterized in that the step of detecting and measuring the light changes comprises detecting the changes of light as said boundary moves between dark and light regions on a series of sequential visual image representations of a dynamically movable structure, and which sequential visual image representations are displayed in sequence at a rate to represent the movable structure during movement thereof.

57. A system for detecting and measuring the area of motion of a dynamically moving structure having a boundary moving between light and dark areas, said system comprising:
 (a) a main photocell for detecting and measuring the light changes in response to a boundary on either said structure or a series of sequential image representations of that structure moving between adjacent dark and light areas on said dynamically moving structure or said series of sequential visual image representations of said structure, said main photocell generating a current representing signal therefrom which is an analog of the motion of the boundary,
 (b) sampling means for sampling an instantaneous amplitude of the signal representing a greatest instantaneous brightness,
 (c) conversion means for converting the current representing signal to a voltage equivalent signal,
 (d) peak detection means operatively connected to said sampling means and enabling said sampling means to hold the signal of highest amplitude thus sampled until an instantaneous amplitude of greater brightness is detected, and using the instantaneous amplitude of greatest brightness to determine maximum movement of the boundary,
 (e) filter means operatively connected to said sampling means for extracting flicker artifact from the signal to thereby provide an analog signal representative of the motion of the boundary,
 (f) a first reference photocell located in proximity to said main photocell for measuring the intensity of the same reflected light measured by the main photocell over the same area thereof,
 (g) a second reference photocell located distal to said main photocell and located over the other of the light or dark areas for measuring the intensity of the light reflected from such other area,
 (h) first amplifier means receiving a signal from the first reference photocell,
 (i) second amplifier means receiving a signal from the second reference photocell,
 (j) third amplifier means receiving a signal from the main photocell, the signals from the second and third amplifier means being coupled, means for dividing the signal from the first amplifier means by a signal resulting from the coupling of the signals from the second and third amplier means, and
 (k) means to receive the signals from the amplifier means and provide a representation of the amount of movement based thereon.

58. The system of claim 57 further characterized in that the output of said sampling means is controlled by a means forming part of said peak detection means.

* * * * *